United States Patent [19]

Enloe

[11] Patent Number: 4,585,448
[45] Date of Patent: Apr. 29, 1986

[54] DISPOSABLE GARMENT HAVING HIGH-ABSORBENCY AREA

[75] Inventor: Kenneth M. Enloe, Winnebago County, Wis.

[73] Assignee: Kimberly-Clark Corporation, Neenah, Wis.

[21] Appl. No.: 683,778

[22] Filed: Dec. 19, 1984

[51] Int. Cl.$^4$ ............................................. A61F 13/16
[52] U.S. Cl. ................................. 604/378; 604/385 A
[58] Field of Search .............. 604/385, 378, 381, 358, 604/368, 369

[56] References Cited

U.S. PATENT DOCUMENTS

| | | |
|---|---|---|
| 2,696,819 | 12/1954 | Lovekin . |
| 2,890,700 | 6/1959 | Loneberg-Holm . |
| 3,063,452 | 11/1962 | Del Guercio . |
| 3,603,314 | 9/1971 | Aberg .................................. 604/381 |
| 3,636,952 | 1/1972 | George . |
| 3,766,922 | 10/1973 | Krusko . |
| 3,924,626 | 12/1975 | Lee et al. ............................ 604/385 |
| 3,926,189 | 12/1975 | Taylor . |
| 4,019,517 | 4/1977 | Glassman . |
| 4,037,602 | 7/1977 | Hawthorne . |
| 4,212,302 | 7/1980 | Karami ............................... 604/368 |
| 4,285,342 | 8/1981 | Mesek . |
| 4,338,938 | 7/1982 | Seavitt ................................ 604/385 |
| 4,381,782 | 5/1983 | Mazurak et al. . |
| 4,501,587 | 2/1985 | Enloe . |

Primary Examiner—John D. Yasko
Attorney, Agent, or Firm—Paul A. Leipold; Donald L. Traut; J. J. Duggan

[57] ABSTRACT

The invention is generally accomplished by providing a disposable garment comprising a liquid impervious backing sheet, a liquid pervious body-side liner sheet, and an integral absorbent pad disposed between the liner and cover sheets. The absorbent pad is provided with a high absorbency area extending from the crotch region toward the center of the front waist of the garment. It is preferred that about 65 percent of the total absorbent be in the front half of the diaper with the about 40 percent of the total in the high absorbency area.

11 Claims, 10 Drawing Figures

DISPOSABLE GARMENT HAVING HIGH-ABSORBENCY AREA

TECHNICAL FIELD

This invention relates to a disposable garment, such as a diaper, having absorbent material positioned to increase absorbent capacity and facilitate folding of the diaper. More particularly, the invention relates to the positioning of additional absorbent material in the front section of the diaper.

BACKGROUND ART

Disposable diapers typically have a substantially rectangular absorbent pad and side portions that are folded toward each other; that is, toward the longitudinal centerline of the diaper and against the pad. However, the fold portions are usually positioned such that the opposing edges of the fold portions do not reach each other, but are spaced apart. Where the fold portions include pad material, a space between the folded edges having a thickness approximately equal to the thickness of the pad material in the fold portions is formed between the fold portions. In those types of diapers in which the pad is shaped or contoured to form a narrower central portion to allow space for the wearer's legs, the volume of the void space between the opposite edges of the fold portions increases substantially. In addition to the longitudinal side portions being folded toward each other and against the central portion of the diaper, for purposes of packaging, the front and rear sections of the diaper are folded into engagement with each other along a transverse line dividing the diaper into front and rear sections. The void spaces between the longitudinal fold portions in the front section and in the the rear section of the diaper are thus combined to form a single larger void space in the fully folded diaper which, to the extent that it is retained after the diaper is placed in a package, is wasted space. To the extent that the folded diaper is compressed to eliminate the void space, the diaper is distorted to decrease absorbent capacity, to detract from the appearance of the diaper and create packaging problems when using automatic high-speed packaging equipment. A related folding problem involves the folding of the side portions, including the absorbent material they contain, consistently along a longitudinal fold line, to provide a uniform width diaper when fully folded. Similar to folding of the front and rear sections of the diaper together, uniform folding of the diaper side portions enhances the appearance of the diaper and minimizes packaging problems.

Another problem which is common to disposable diapers is the need for increased fluid absorbent capacity. One of the areas of the diaper at which it is particularly important to have a large amount of absorbent capacity is in the front portion of the diaper because this is the area normally directly wetted by infants and because of the tendency of urine to flow to this area of the diaper when the baby is crawling or sleeping. There have been a wide variety of suggested solutions for increasing the absorbent capacity of the diaper in general and increasing the absorbent capacity of the diaper in the frontal region in particular. Typical of these is the arrangement illustrated in U.S. Pat. No. 3,926,189 to Taylor. This patent discloses a main pad having an auxiliary portion extending from the main pad at approximately the transverse centerline of the diaper. The auxiliary pad portion may be folded forward to the front area of the diaper when the baby is in a sleeping position or the diaper is to be worn by a boy baby to thereby gain the increased front absorbent capacity.

It has been disclosed in U.S. Ser. No. 430,621—Enloe—filed Sept. 30, 1982, now U.S. Pat. No. 4,501,587 having common assigment and inventor, that a particularly desirable diaper can be formed by placing one or two auxiliary pad(s) into the front of the diaper such that the diaper may be formed with increased absorbency but nevertheless be still folded in about the same thickness for packaging. However, there remains a need for a diaper with increased absorbency in the front portion that is particularly convenient and low cost to commercially form.

DISCLOSURE OF THE INVENTION

An object of this invention is to provide an optimum distribution of absorbent in a disposable garment such that the absorbent will be utilized effectively by the wearer but not provide a bulky garment.

Another object of this invention is to provide a low-cost method of forming a disposable garment having a high-absorbency region.

An additional object of this invention is to provide an absorbent disposable garment that has minimum leakage and maximum use of absorbent.

These and other objects of the invention are generally accomplished by providing a disposable garment comprising a liquid impervious backing sheet, a liquid pervious body-side liner sheet, and an integral absorbent pad disposed between the liner and cover sheets. The absorbent pad is provided with a high absorbency panel extending from the crotch regions toward the center of the front waist of the garment. It is preferred that about 65 percent of the total absorbent be in the front half of the diaper with the about 40 percent of the total in the center front high absorbency panel.

DETAILED DESCRIPTION OF THE INVENTION

The diaper of the invention has numerous advantages over prior diapers. The invention allows the formation of a diaper having an area of high absorbency that to the casual observer or user does not appear to be undesirably thick and heavy in one area. The diaper may be folded flat for convenient packaging and storage without wasting large volumes of space. The diaper is less subject to leakage than previous diapers. The diaper is low in cost to form as the absorbent may be formed in a single step much as previous absorbent pads of diapers without high-absorption areas were formed. These and other advantages will be apparent from further description of the invention below.

U.S. patent application Ser. No. 430,621 filed Sept. 30, 1982, now U.S. Pat. No. 4,501,587 inventor Kenneth M. Enloe, incorporated by reference herein, discloses a diaper that uses one or two auxiliary pads to made an area of high absorbency in the front of the diaper. It is disclosed therein that the auxiliary pad(s) is generally a separate piece(s) of absorbent that is placed onto an underlying layer of absorbent to increase the absorbency in the front area while still allowing folding and compact stacking of the diaper. It is also disclosed therein that the auxiliary pads may be formed as an integral unit. It has now been found that a novel and particularly preferred method of forming a diaper with an entire integral pad is possible with careful control of the amount of absorbency of the front half of the diaper and particularly the amount of absorbent in the high-absorbency area of the center front panel between the diaper's folds. The invention further provides a diaper having a middle back panel of higher absorbency than the wings (outer thirds) of either the back or front of the diaper. Further, it has been found that the high-absorbency area is suitable for use with an elastic waist diaper for improved performance. These and other advantages of the invention will become apparent from the detailed description below.

Figure 1:
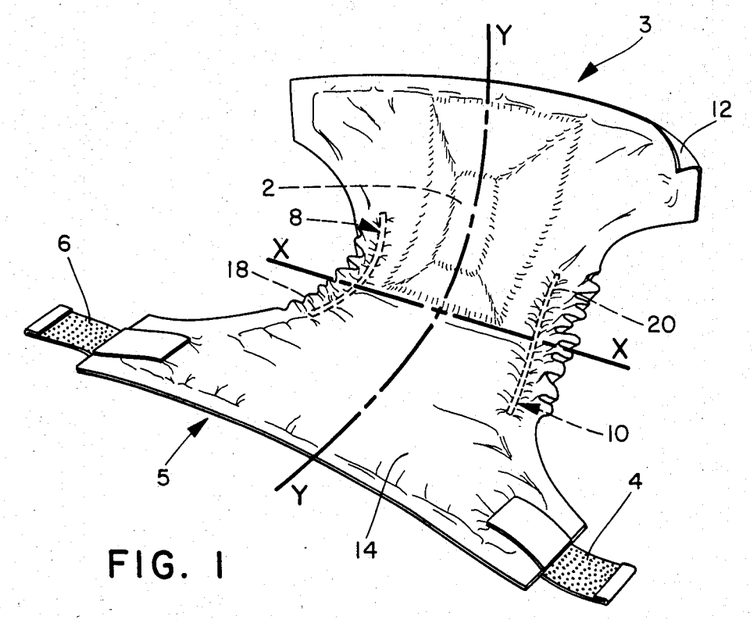
FIG. 1 is a perspective view of a disposable diaper.
Figure 1A:
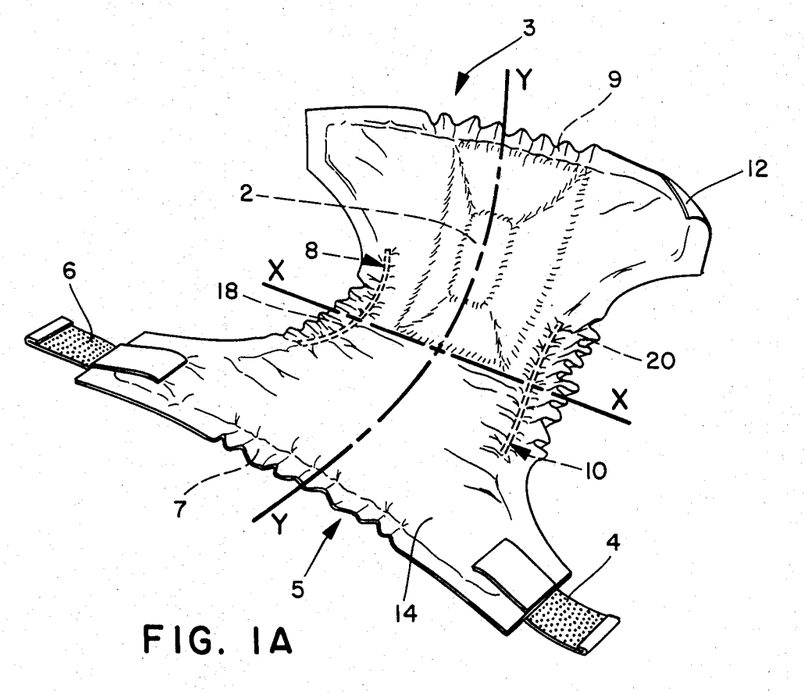
FIG. 1A is a perspective view of a diaper of the invention having an elastic waist.

With reference to drawings, the disposable diaper shown in FIGS. 1 and 1A is in an unfolded condition ready to be fitted to the wearer. The disposable diaper is shown as having a main pad assembly 2 and a pair of waist fastening tapes 4 and 6. As shown in the embodiments of FIGS. 1 and 1A, the diaper also has leg elastic means 8 and 10 as well as waist elastic 7 and 9 in FIG. 1A.

As shown in FIGS. 1 and 1A, the diaper has a longitudinal centerline Y—Y. The transverse centerline X—X running through the crotch section delineates the front section 3 from the rear section 5 of the diaper. Both fastening tapes 4 and 6 are shown in FIGS. 1 and 1A in extended condition ready to be attached to the front section 3 of the diaper when it is placed on the wearer. Leg elastic means 8 and 10 comprise lengths of elastic material 18 and 20 attached to the outer cover sheet 12 or the liner sheet 14 or both, and positioned between the cover sheet and the liner sheet substantially parallel to the longitudinal centerline Y—Y of the diaper.

Figure 2:
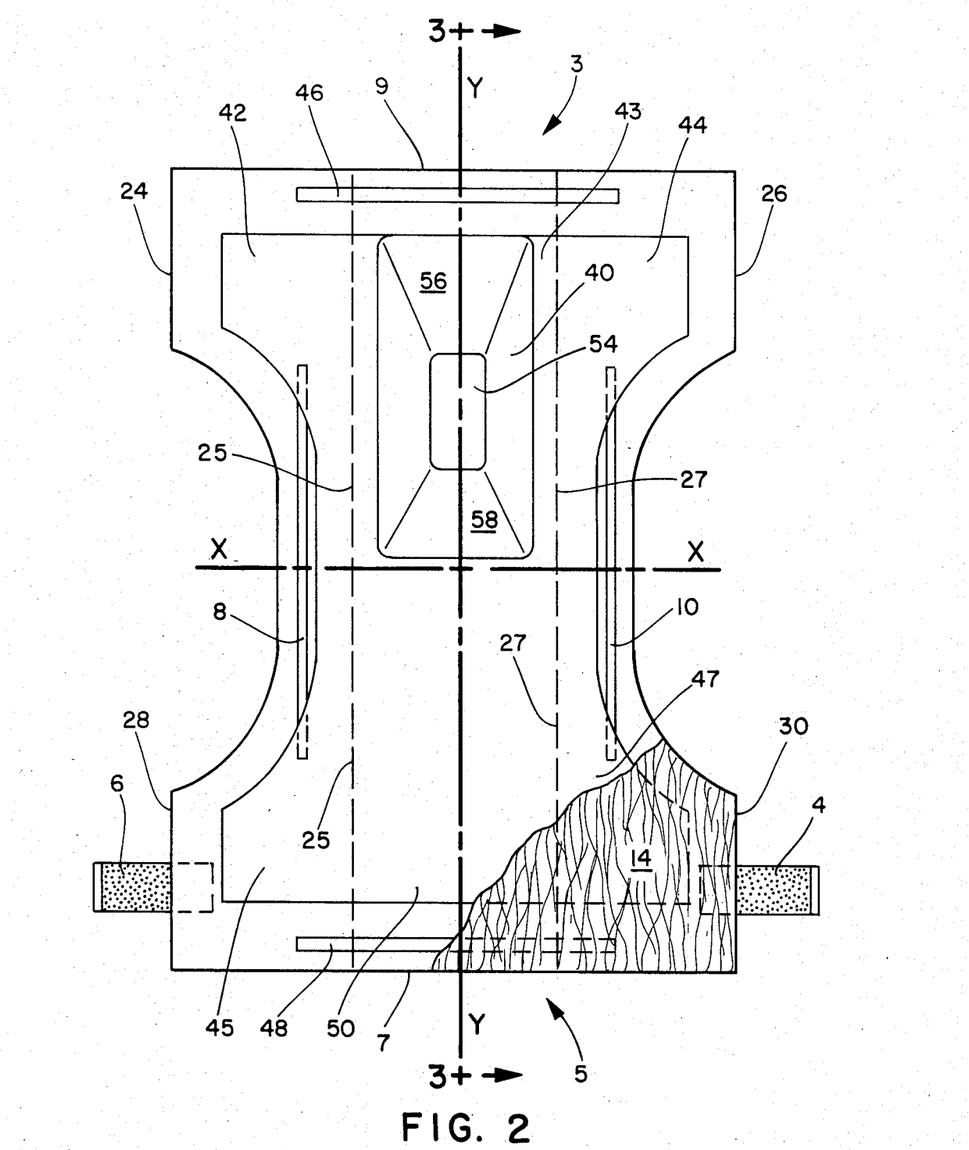
FIG. 2 is a plan view of a disposable diaper in accordance with the invention.
Figure 3:
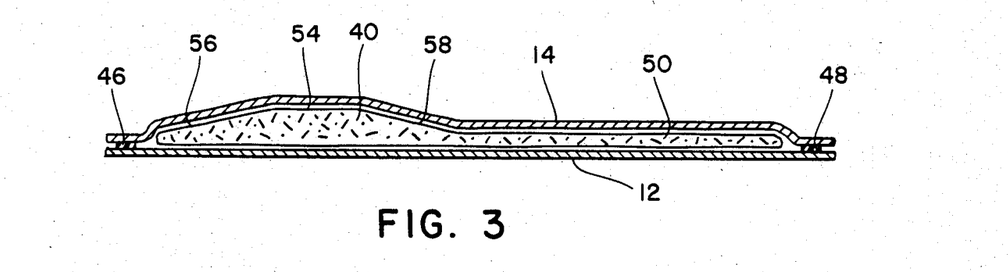
FIG. 3 is a cross-section along line 3—3 of FIG. 2.

With reference to FIGS. 2 and 3 of the diaper, the front of the diaper has a thicker high absorbency area 40 centered in the front 3 and extending from the center crotch fold shown by X—X to almost the edge of the front portion of the absorbent pad. The front portion has high basis weight and high-absorbency area 40 in the front center panel 43 of the diaper and lower basis weight hence lower-absorbency areas 42 and 44, forming the less absorbent-containing ears of the diaper which are lapped around the sides of the wearer in use. The diaper as shown has waist elastic 46 in the front of the diaper 3, forming elasticized area 9. The back of the garment has elastic 48 forming elasticized areas 7 when the diaper elastic is in relaxed condition. It is noted that in FIG. 2 the diaper is in extended condition. The absorbency of the center panel of the back of the diaper 50 is preferably generally higher than the wings or ears 28 and 30.

The wings or ear portions 42 and 44 in the front and 45 and 47 in the back of the diaper have less absorbency than the center back panel or the center front panel. The center back panel 50 preferably has less absorbency than the front center panel 43. The fold lines 25 and 27 are the dividing lines for the center panels and ear panels. The center panels 43 and 50 are slightly wider than a third the width of the diaper. However, the proportion of absorbent is greater in the center panels 43 and 50, both because the absorbent is preferably thicker there and because the width of the absorbent in the ears 42, 44, 45 and 47 is much less than that in the middle section of the diaper as the absorbent does not extend to the edge of the diaper. The diaper may be considered as having six sections or panels. The front of the garment or diaper 3 has a center high absorbency panel 43, and two wings or ears 24 and 26. The garment back 5 has center back panel 50 of greater absorbency than the wings 28 and 30. As used herein, the back of the garment is the portion that is worn on the back of the wearer and the front of the garment is the portion worn on the front of the wearer. It is noted that the high-absorbency area 40 of front panel 43 has a centered portion 54 of greatest thickness with gradually raising areas 56 and 58. The illustration of FIG. 2 further shows the fold lines 25 and 27 that are utilized to fold the ear portions of the diaper 24 and 26 over the less thick portions of the high-absorbency area 40. The back ear portions 28 and 30 also are folded simultaneously at this time along the fold lines 25 and 27.

Figure 6:
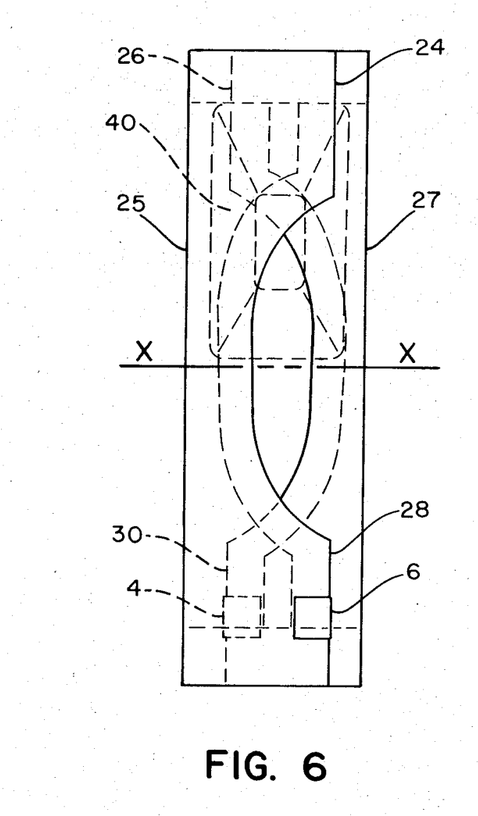
FIG. 6 is a plan view of a diaper in accordance with the invention after the sides are folded.

FIG. 6 illustrates the diaper after the ears 24, 26, 28 and 30 have been folded. It is noted that the diaper tapes 4 and 6 are in their closed positions when the diaper is folded. Also shown is the outline of the higher absorbent portion 40 of the diaper.

Figure 4:
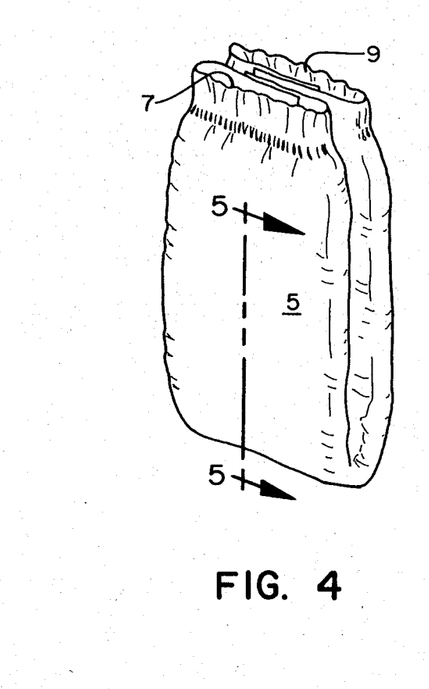
FIG. 4 is a perspective view of a folded diaper in accordance with the invention.
Figure 5:
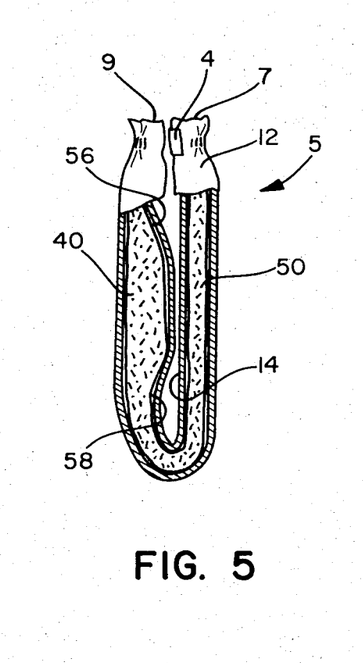
FIG. 5 is a side elevational view of a partial and cross-section on line 5—5 of the diaper in FIG. 4.

FIGS. 4 and 5 illustrate the completely folded garment of the invention as it would be folded for packaging. In the cross-sectional view of FIG. 5 it is seen that the high-absorbency area 40 is adapted to be placed between the folded absorbent portions of ears 26 and 24 so as to form a compact package.

Figures 7, 8:
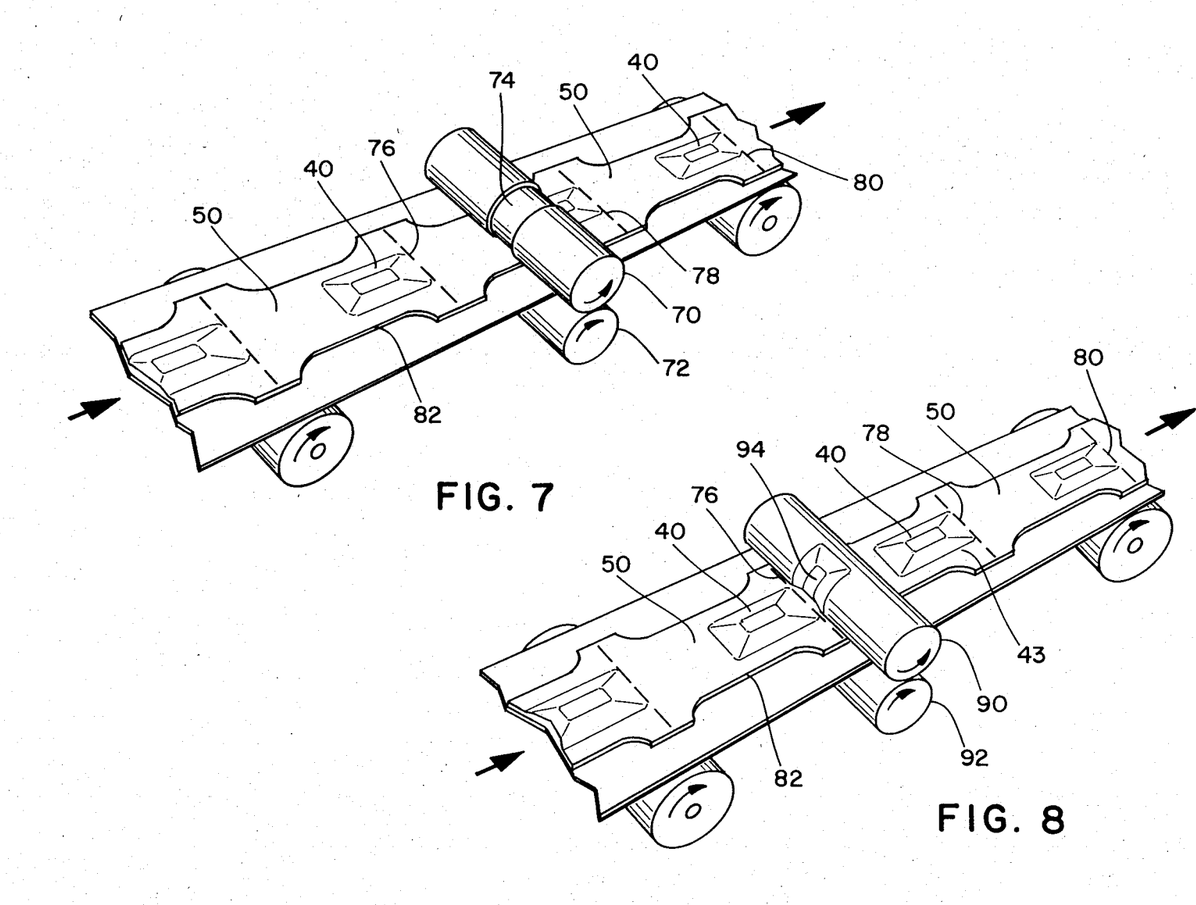
FIG. 7 is a perspective view of a portion of a debulking line for the absorbent pads in the invention.
FIG. 8 is a perspective view of a portion of apparatus for debulking pads of the invention in which the debulking rolls are indented in the area of greater absorbency.

As is illustrated in FIGS. 7 and 8 the absorbent member 50 was formed on a air-former that has an indentation allowing the build up of a larger portion of fluff in the area 40 of the front panel 43 where the high-absorbent area is to be formed. The center back panel is preferably formed with a higher absorbency than the wings. The absorbent 50 after leaving the former (not shown) is passed onto a belt where debulking compression rolls 70 and 72 compress the material to provide it with more strength and to debulk it for easier handling in the diaper. The formation of air formed fibrous panels of varying thickness are known in the art. Typical of such formation techniques are those of U.S. Pat. Nos, 4,005,957—Savich, 4,016,628—Kolbach and 4,388,056—Lee et al. The formation may be carried out by any desired technique. It is noted that the roll 70 has an area 74 that is slightly indented in the area where the high-absorbency material is located. This offset or indentation is a relatively small deviation from the surface level of the roll generally being only about 0.1 inch. The pile of fluff from the high-absorbency area is about 2 inches prior to compression. Distance between the debulking rolls 70 and 72 is about 0.15 inches in the offset areas and about 0.05 inches in the remainder of the rolls.

After compression the connected pieces of absorbent are severed at lines 76, 78, and 80, and assembled into the diaper in a conventional manner. It is noted that the leg cutouts 82 may be formed either prior to compression or they may be cut out after compression if the pad is not formed initially in the shape of the absorbent pad desired. In FIG. 8 a similar system is illustrated except that the debulking rolls 90 and 92 are provided with a cavity 94 that corresponds to the high-absorbency areas. The use of the roll that has the indentations is preferred for diaper optimum performance. The depth of the indentations or cavities below the roll surface is preferred to be about 0.1 inch for the best combination of compact folded diaper and good absorbency. The distance between the rolls 90 and 92 in other areas is about 0.05 inches. However, the performance with the uniform centered roll has been found to be almost as good and the processing is much simpler as the roll does not need to be calibrated closely with the fluff being carrier beneath it.

Figure 9:
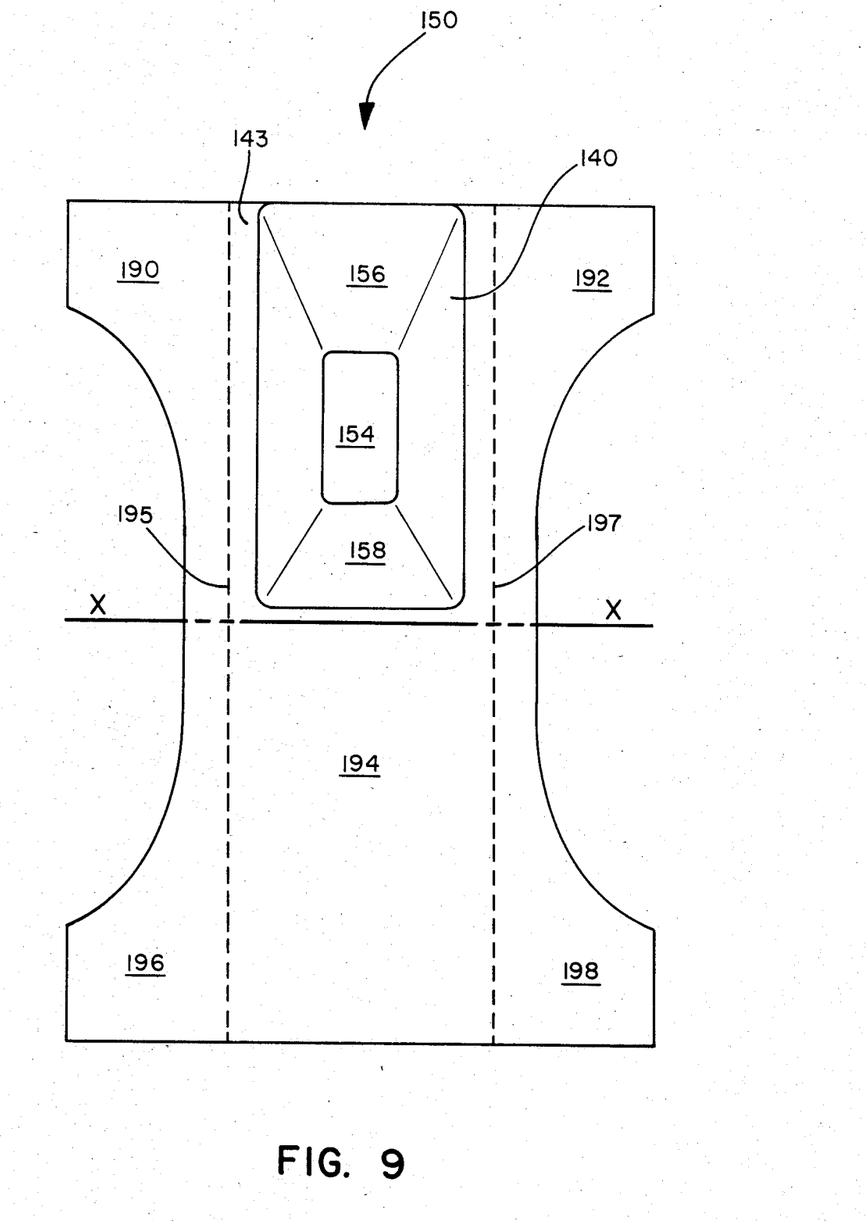
FIG. 9 is a plan view of the absorbent in accordance with the invention with panels of absorbency indicated.

As is illustrated in FIG. 9 the absorbent pad 150 having the highest-absorbency area 140 in front center panel 143 is composed of the area of greater absorbency 154 with gradient areas 156 and 158 blending into the lower-absorbent areas that will be the ears 190 and 192 of the front, and also blending into the lesser absorbency back portions 194, 196 and 198. The fold lines will be at areas 195 and 197, with the crotch fold along line X—X. The back of pad 150 is made up of a higher absorbency center panel area 194 and lower absorbency areas 196 and 198.

The amount of the diaper absorbent in the front high-absorbency area may be any desired effective amount. It is generally preferred that the high-absorbency area has between about 30 percent and about 50 percent of the total absorbency of the diaper. It is particularly preferred that the amount of absorbent in the high-absorbency area be about 40 for best performance, particularly in a diaper intended for nighttime use. The preferred amount of absorbent in the center back panel is between about 20 and about 30 percent of the diaper's total for best absorbency and folding. The garment's ears each have between about 5 and about 10 percent of the total wood fluff for good fit and folding.

The preferred amount of extra absorbency gives an amount of about 35 percent of the total absorbent in the back of the diaper, and about 65 percent of the total absorbent in the front, with the absorbent in the front preferably divided such that of the 65 percent in the front, about 40 percent is in the center front panel extra-absorbency area and about 15 percent as the combined total of the front wings.

The integral pad with extra-absorbency area is suitable for use as the absorbent in a diaper that has no elastic, a diaper that has elasticized legs, or a diaper that has elastic legs and also an elasticized waist. It is particularly suitable for a diaper with an elasticized waist and legs as it offers absorbency in the front area for absorption of liquid that is contained by the elastic waist when the wearers are sleeping on their stomachs.

The preferred material for the absorbent of the garment is fluff that is divellicated wood pulp. Generally it is preferred that the height or thickness of the area of high absorbency be between about 0.5 and about 0.8 inch after debulking, with the ears of the front of the diaper and the back of the diaper having a height of about 0.2 to 0.5 inch. It is quite surprising that the extra absorbency can be so effective with only the small 0.3 to 0.6 inch difference in height between the lesser absorbent wings and the extra absorbent front center panel areas after debulking. The larger size differences would be in the large toddler size diapers.

The length of the higher absorbency area within the center front panel is generally between about 9 and about 5.5 inches, with the larger length being in the toddler-size diaper and the small in the newborn diaper. The preferred width of the extra absorbency area with the center front panel is about 2.5 to about 4.5 inches. However, it noted that the width of the extra absorbency area is dependent on the fold lines of the particular diaper. The high absorbency area preferably is less than the width between the fold lines in order to result in a compact folded diaper. The width of the center panel is generally between about 4 and about 5 inches. The total weight of absorbent develicated cellulose fluff in a newborn size diaper generally is about 30 grams dry weight. The weight of wood fluff absorbent in a medium diaper typically is about 45 grams dry weight and the dry weight in a toddler is typically about 57 grams. As discussed below, an equivalent amount of absorptive capacity could be achieved using other materials that would have a different dry weight of absorptive material.

The wood fluff may be formed by a vacuum on a forming drum with vacuum of about 25 inches of water. The screen on the forming drum is indented to form the thicker areas where desired. Depth of fluff in the extra absorbency area is generally between about 1½ and 2½ inches prior to compaction. The depth in the other areas prior to compression by the debulking rolls is between about ½ and about ¾ inch. It is preferred that the height of fluff in the extra absorbency area be between about 1¾ and about 2 inches prior to debulking for best high absorbency and good fit.

While the highest absorption area in the center front has been described as thicker and containing more absorbent wood fiber, it is possible that the higher zones of absorbency could also alternatively be formed by use of zoned superabsorbent materials. Such a diaper could have a proportionally thinner pad and a lower weight of wood pulp fluff or could have a single thickness pad but be provided in the front center panel and to a lesser degree in the rear center panel with superabsorbent material to increase the absorbency in those areas without the absorbent being significantly thicker. Typical of superabsorbent materials are water insoluble hydocolloidal particles derived from starches that will swell but not dissolve when exposed to water. Other superabsorbents are formed from hydrolyzed cross-linked polyacrylates, polyacrylamides, polymers of acrylic polymers and salts and copolymers thereof. While the term "weight of absorbent" and "amount of absorbency" may be used as equivalents for the wood fiber absorbent, this is not true for superabsorbent containing articles. The dry weight, and liquid holding ability for superabsorbent containing materials are not equivalents when part of the absorbency of the garment is the result of the superabsorbent that absorbs a greater amount of liquid for the same dry weight than does wood fluff.

As illustrated above, the invention provides a desirable diaper with a high-absorbency area that has an ease of formation, good appearance, and folding properties. While the invention has been described in conjunction with specific embodiments thereof, it is evident that many alternatives, modifications in variations should be apparent to those skilled in the art in light of the foregoing description. For instance while described with infant diapers the invention also could be used with incontinent garments. Accordingly, it is intended to embrace all such alternatives, modifications and variations as fall within the spirit and scope of the appended claims.

I claim:

1. An absorbent garment comprising an impervious backing, a permeable body side lining and an absorbent between said impervious backing and said body side lining, said garment divided into six panels by folds, the front of the garment divided into a front center panel and two side ears, the back divided into a back center panel and two side ears wherein said back and front ears have between about 20 and up to 40 percent of the absorbency of said garment, said front center panel has between about 30 and about 50 percent of said absorbency of said garment and said back center panel has between about 20 and about 30 percent of said absorbency and wherein between about 25 percent and about 45 percent of the total absorbency is in the back of the diaper.

2. The garment of claim 1 wherein said center front panel is formed by compression of a pile of vacuum formed fluff about 2 inches in height prior to compression.

3. The garment of claim 1 wherein each of the four ears of said diaper has between about 5 and up to 10 percent of the absorbency of said garment.

4. The garment of claim 1 wherein said absorbent is arranged such that between about 55 and about 75 of said absorbent capacity is in the front half of said garment.

5. The disposable garment of claim 1 wherein said absorbent is wood fluff between about 0.5 and about 0.8 inch thickness in the front center panel.

6. The garment of claim 1 wherein said garment further comprises an elasticized waist.

7. The garment of claim 1 wherein said absorbent is formed as an integral layer develicated wood fluff that is compressed to between about 0.5 and about 0.8 inch thick along the centerline and between about 0.2 and about 0.4 inch thick along the edges.

8. The garment of claim 1 wherein between about 10 percent and about 20 percent of total absorbency is in the ears on the front of said garment outside of said center front panel high-absorbency region.

9. The garment of claim 1 wherein said absorbent is wood fluff between about 0.5 and about 0.8 inch thick in said center front panel and between about 0.2 and about 0.5 inch thick in the remainder of said garment with a height difference between the fluff in the ears of said garment and said center front panel of between about 0.3 and about 0.6 inch.

10. The garment of claim 1 wherein the absorbent area of said front center panel has a length of between about 9 and about 5.5 inches and a width of between about 4 and about 5 inches.

11. The garment of claim 1 wherein said center front panel comprises superabsorbent.

* * * * *

UNITED STATES PATENT AND TRADEMARK OFFICE
CERTIFICATE OF CORRECTION

PATENT NO. : 4,585,448
DATED : April 29, 1986
INVENTOR(S) : Enloe

It is certified that error appears in the above-identified patent and that said Letters Patent are hereby corrected as shown below:

Column 2 line 6 "assigment" should read "assignment"

Column 2 line 54 should read ...of the invention.

Column 5 line 20 "carrier" should read "carried"

Signed and Sealed this

Fourth Day of November, 1986

[SEAL]

Attest:

DONALD J. QUIGG

Attesting Officer     Commissioner of Patents and Trademarks